United States Patent [19]

Babior

[11] Patent Number: 4,923,797

[45] Date of Patent: May 8, 1990

[54] STABILIZATION OF LEUKOCYTES

[75] Inventor: Bernard M. Babior, San Diego, Calif.

[73] Assignee: President & Fellows of Harvard College, Cambridge, Mass.

[21] Appl. No.: 277,256

[22] Filed: Nov. 29, 1988

[51] Int. Cl.$^5$ ........................ A01N 1/02; A61K 35/14
[52] U.S. Cl. ........................................ 435/2; 424/534
[58] Field of Search ............................ 435/2; 424/101

[56] References Cited

U.S. PATENT DOCUMENTS

| 3,874,384 | 4/1975 | Deindoerfer et al. |
| 4,356,172 | 10/1982 | Nakao et al. |
| 4,539,204 | 9/1985 | Ecanow et al. |
| 4,558,032 | 12/1985 | Ecanow et al. |
| 4,596,788 | 6/1986 | Ecanow et al. |
| 4,639,373 | 1/1987 | Babior. |
| 4,663,058 | 5/1987 | Wells et al. |

OTHER PUBLICATIONS

Tal'skaya et al.–Chem. Abst., vol. 67 (1967) p. 30367a.
Gaenshirt–Chem. Abst., vol. 74 (1971) p. 29993q.
Kummer et al., Vox Sanguinis, vol. 24, pp. 76–88 (1973).
Rock, Gail, Journal of Clinical Apheresis, vol. 2, pp. 63–67 (1984).
Rock et al., Transfusion, vol. 24, pp. 68–73 (1984).
Huestis et al., Transfusion, vol. 25, pp. 343–348 (1985).
Lefrancois, Transfusion, vol. 27, pp. 112–113 (1987).
Stibbe et al., Haemostasis, vol. 10, pp. 276–288 (1981).
Tomono et al., Vox Sanguinis, vol. 51, pp. 81–86 (1986).
Price et al., Transfusion, vol. 25, pp. 238–241 (1985).
Cronstein et al., J. Clin. Invest., vol. 78, pp. 760–770 (Sep. 1986).

*Primary Examiner*—Sam Rosen
*Attorney, Agent, or Firm*—Fish & Richardson

[57] ABSTRACT

Preservation of leukocytes by suspending in storage medium containing modified fluid gelatin, plasma, and a non-toxic buffer. Preferred additives include heterocyclic bases which occur in nucleic acids, or nucleosides or nucleotides containing the same.

7 Claims, No Drawings

STABILIZATION OF LEUKOCYTES

This invention relates to the storage of human white cells or leukocytes and pertains more specifically to a composition containing human plasma, modified fluid gelatin, and non-toxic buffer, into which leukocytes can be dispersed and stably maintained during storage at low temperature for periods of at least 24 hours, usually at 48 hours, and even up to two weeks or more. Improved results can be achieved by including also in the composition one or more of (a) heterocyclic bases (purines or pyrimidines) which occur in nucleic acids; (b) nucleosides containing said bases; or (c) nucleotides containing said bases. Among suitable heterocyclic bases are adenine, cytosine, guanine, thymine and uracil.

While collection and fractionation of human blood and use of its components for transfusion is widely practiced, use of certain components such as granulocytes or polymorphonuclear leukocytes has been severely limited by the lack of stability of these components during storage, even at 4° C. This lack of stability is manifested primarily by agglutination or clumping of the cells and also involves acceleration of the cell death rate and reduction of bactericidal capacity of the cells. As a practical matter, these difficulties have greatly restricted the use of such components, since distribution and supply of blood components to points of need require that the components be stored for substantial periods of time up to two weeks or even more.

Moreover, additional storage time would allow additional tests to be carried out such as HLA typing or cross-matching or tests for the presence of cytomegalovirus and other pathogens, thus optimizing benefits of the transfusion procedure.

It has hitherto been proposed to employ plasma and gelatin in a buffer for storage of granulocytes as described in Babior et al. U.S. Pat. No. 4,639,373.

It has now been found that substantially longer storage and less degradation of leukocytes during storage at temperatures below 25° C., preferably below 8° C. but above freezing, can be achieved by employing in combination plasma, modified fluid gelatin, and a physiologically acceptable non-toxic buffer. Modified fluid gelatin has been used clinically as a plasma substitute or expander and is widely available under a variety of trade names, such as PlasmaGel, Haemaccel, Leukogel, Gelofusine, etc. In general, these materials are partly hydrolyzed gelatins which have an average molecular weight from 15,000–40,000 daltons and which form aqueous solutions having a viscosity less than that of a gelatin solution of the same concentration. In some cases they are succinylated, or they are reacted to form e.g. urea linkages, or cross-linked. The commercially available materials usually are in the form of a solution of the modified gelatin in a buffer together with various salts and other ingredients. The term "modified fluid gelatin" as used herein refers to the partly hydrolyzed gelatin component itself whether or not further reacted. In some cases the commercially available solutions can be used, but preferably the partly hydrolyzed gelatin component is purified by separation from the remaining ingredients of the commercial product.

Any conventional buffer solution can be used in the compositions of the present invention such as any of the buffers commonly used in connection with storage of blood or its components at a pH from 4 to 7.5, e.g., Citrate Phosphate Dextrose (CPD) which consists of 2.06 grams citric acid, 16.6 grams sodium citrate, 16.1 grams dextrose and 1.40 grams monobasic sodium phosphate dissolved in deionized water to make 630 ml; or Acid Citrate Dextrose (ACD) which consists of 14.75 grams citric acid, 29.0 grams sodium citrate, and 20.0 grams dextrose dissolved in deionized water to make 500 ml. The ACD buffer is preferred because compositions made with it maintain better the bacterial killing activity of the leukocytes during storage.

The heterocyclic base component (free base, nucleoside, or nucleotide), when present, may be present in very small concentrations, as little as about 0.001 mM being effective to enhance stability of leukocytes dispersed in the compositions, but the preferred concentration range is from 0.5 to 3 mM in the composition.

The plasma present in the composition may be normal human plasma, either autologous or heterologous with the leukocytes, preferably autologous. The amount of plasma present in the composition must be at least 25% by weight based on the total composition exclusive of the leukocytes, while the preferred amount is from 40 to 50% by weight. Larger amounts of plasma up to about 75% by weight can be used.

The amount of modified fluid gelatin in the composition may vary considerably, from 4% by weight based on the total composition, exclusive of leukocytes, up to the amount which causes the composition to set to a gel at 40° C. The amounts required for optimum results vary depending upon the source of the modified fluid gelatin but can readily be determined in any given case by a simple test.

The leukocytes can be dispersed in the composition in amounts varying from $10^7$ to $10^9$ cells per ml, preferably from $1 \times 10^8$ to $5 \times 10^8$ cells per ml.

During storage of the leukocyte-containing composition, it is preferably maintained at a temperature below 8° C. although higher temperatures up to 25° C. can be tolerated for relatively short times. For optimum storage life, storage temperature should be maintained at 4° C. or lower, but not below freezing temperature.

After storage the composition containing the leukocytes can be transfused after warming without further processing; or if desired the leukocytes can be separated from the composition by washing or centrifuging in order to permit dispersion of the cells in any other desired medium.

It is contemplated that the present invention may be practiced by supplying to blood banks, laboratories or other entities a stock solution suitable for mixing with a suspension of leukocytes in plasma, free from red cells, with directions for mixing the stock solution with the suspension in suitable proportions. Such a stock solution comprises a water solution containing an amount of modified fluid gelatin from 8% by weight up to the amount causing the solution to gel at room temperature, preferably 20 to 40% by weight, and a member of the group consisting of (a) the heterocyclic bases which occur in nucleic acids, (b) nucleosides containing said bases, (c) nucleotides containing said bases, and (d) mixtures of (a), (b) and (c), said member being present at a concentration from 0.5 micromolar to 10 millimolar, preferably from 0.8 to 8 millimolar. The member preferably is adenosine or guanosine. The stock solution may also include a non-toxic buffer at a pH of 4–7.5, preferably a citrate-based buffer such as ACD or CPD at a concentration of 100–500 milliosmoles per liter.

The following specific examples are intended to illustrate the invention without acting as a limitation upon its scope.

In each case of the following examples the plasma employed was prepared by drawing 20 ml of whole blood into a 30 ml syringe preloaded with either 4 ml ACD buffer or with 2.8 ml CPD buffer, then spinning for ten minutes at 2,000 rpm in a centrifuge at 4° C. The supernatant was separated and used as plasma.

The leukocytes (neutrophils) used in these examples were prepared from whole human blood by drawing a 30 ml specimen of blood into a 60 ml syringe pre-loaded with 6 ml ACD buffer; to the mixture was added 20 ml of 6% dextran (GENTRAN 70, Pharmacia) in normal saline (0.9%), and after standing, the straw colored supernatant was separated and spun ten minutes at 800 rpm in a centrifuge at 4° C.; the resulting pellet was resuspended in 3.5 ml Dulbecco's Phosphate Buffered Saline without calcium chloride and without magnesium chloride (DPBS--). Four such resuspensions were combined in a centrifuge tube, vortexed, then spun 4 minutes at 1200 rpm at 4° C. in a centrifuge and the supernatant discarded. The red cells were lysed by directing onto the pellet a 6 ml stream of ice cold deionized water, vortexing for 30 seconds, then quickly adding to the suspension 2 ml of 0.6M potassium chloride solution and 3.5 ml DPBS--. The tube was then spun 4 minutes at 800 rpm at 4° C., the supernatant discarded, and the pellet washed gently with 3.5 ml DPBS--. The lysis, washing and spinning was repeated, after which the pellet was resuspended in 3.5 ml DPBS--, pooled with a second pellet prepared in the same manner, and DPBS-- added to a total volume of 20 ml; the suspension was underlaid with 10 ml Ficoll Hypaque, and the tube was spun 20 minutes at 1200 rpm. After removing and discarding the liquid layers, the pellet remaining was resuspended in 2.5 ml of autologous plasma prepared as described above, and the concentration was adjusted to $2 \times 10^8$ cells per ml, twice the concentration desired in the finished storage composition of the example.

The modified fluid gelatin of each example was prepared by purifying commercially available material supplied under the specified trade name by dialyzing exhaustively against water, then lyophilizing. It was then dissolved, for those examples using ACD as the buffer, in the buffer at a concentration such that, after mixing with plasma, the resultant storage solution would have the desired concentration, then mixed with the desired volume of leukocyte-containing plasma prepared as described above and containing the corresponding buffer to form the specimen of storage composition. Where desired, nucleoside bases, nucleosides, and nucleotides were dissolved in the modified fluid gelatin solution before mixing with plasma.

In making storage compositions containing CPD buffer with no heterocyclic base component, the buffer was diluted at 7 parts CPD to 3 parts water before dissolving the modified fluid gelatin in it. When heterocyclic base component was dissolved in addition to the modified fluid gelatin, the buffer was diluted at 6 parts CPD to 4 parts water before dissolution, and both the modified fluid gelatin and heterocyclic base component were dissolved in the diluted buffer to provide the concentration desired in the ultimate storage composition after mixing with plasma.

Storage compositions having the components shown in Tables 1-3 below were prepared by the foregoing procedures, the concentration of modified fluid gelatin and the approximate concentration of plasma in each case being expressed as percentage by weight of the total composition excluding leukocytes.

After storage for seven days at 4° C., the cell recovery (cell count expressed as a percent of initial cell count), cell viability, and bacterial killing power of the cells were determined. These values were determined by bringing the storage sample up to room temperature, spinning 5 minutes at 800 rpm, discarding the supernatant, and resuspending the pellet in 0.6 ml DPBS--; 10 μL of the suspension was diluted in 20 ml of Isoton and counted to determine recovery.

To determine viability, a drop of the resuspension was mixed with an equal volume of 0.2% Trypan Blue in normal saline and incubated 5 minutes at room temperature, after which 100 cells were counted microscopically (blue stained cells were non-viable). The remainder of the resuspension was used for bacterial killing assay.

The bacterial killing assay was conducted using a clinical isolate of *S. aureus* from a patient. The isolate was suspended in Hank's Balanced Salt Solution at a concentration of $1 \times 10^8$ organisms/ml. Autologous serum for use in the assay was prepared by allowing a 5 ml specimen of whole blood to clot for an hour in a culture tube; the clot was loosened, and the tube spun for 10 minutes at 3000 rpm at room temperature. The supernatant was drawn off and used as the serum.

Duplicate assays were conducted for each example by first diluting the resuspension described in the preceding paragraph to a concentration of $2 \times 10^7$ cells per ml, then mixing with serum and buffer in the following proportions to form a test specimen:

200 *S. aureus* suspension at $1 \times 10^8$ bacteria/ml 50 Autologous serum 200 test sample at $2 \times 10^7$ cells/ml in DPBS-- Blanks (controls) were run containing DPBS-- with no neutrophils.

A 100 μl aliquot of each test specimen was diluted immediately 1:10 with DPBS-- to facilitate counting, and the remainder was incubated for 2 hours at 37° C. with gentle but thorough agitation. At the end of the incubation, an additional 100 μl aliquot of each specimen was diluted 1:10 with DPBS--. Each of the two dilutions (and two corresponding dilutions of the blanks) was subjected to the following procedure to determine the proportion of surviving bacteria. A 10 μl aliquot of each dilution was mixed with 4 ml sterile deionized water, sonicated 2-3 seconds to break up clumps, and allowed to stand 5 minutes at room temperature. Top agar was prepared by mixing with Nutrient Broth 0.65% by weight of agar, autoclaving to dissolve, then maintaining at 50° C. A 10 microliter portion of the sonicated solution was added to 5 ml of top agar at 50° C. and poured over a 1.5% nutrient agar plate and allowed to solidify at room temperature, after which the plate was inverted and incubated overnight at 37° C. The colonies were then counted over a light box. Bacterial killing was calculated as follows:

$$\text{Percent kill} = 100 - \left( \frac{\text{surviving bacteria in test specimen}}{\text{surviving bacteria in blank}} \right) \times 100$$

Normal percent kill for fresh leukocytes before storage is ≧90%.

The results are shown in Tables 1, 2 and 3 below:

trieval was facilitated by diluting the storage composition with an equal volume of phosphate-buffered saline, which reduced viscosity and facilitated accurate pipet-

TABLE 1

| Effect of Modified Fluid Gelatin Concentration and Buffer Composition (ACD vs. CPD) | | | | | | | | | | |
|---|---|---|---|---|---|---|---|---|---|---|
| Modified Fluid Gelatin | Plasma | | Buffer | Adenosine | | Leukocyte Recovery % | | Viability % | | Bacterial Kill |
| Brand | % of Total | %* of Total | | (mM) | No. of Samples | | SE** | | SE | | SE |
| Plasma-gel | 12 | 45 | ACD | 0 | 12 | 72.1 | 4.9 | 66.6 | 5.3 | 68.3 | 4.8 |
| | 9 | 45 | ACD | 0 | 3 | 70.7 | 6.2 | 65.0 | 8.8 | 36.7 | 10.4 |
| | 6 | 45 | ACD | 0 | 3 | 73.3 | 4.3 | 72.7 | 4.4 | 21.8 | 5.6 |
| | 3 | 45 | ACD | 0 | 3 | 66.0 | 2.5 | 63.0 | 8.2 | 21.7 | 3.0 |
| | 0 | 45 | ACD | 0 | 12 | 41.6 | 4.3 | 78.3 | 2.2 | 15.5 | 3.6 |
| | 12 | 45 | CPD | 0 | 6 | 62.7 | 7.4 | 81.8 | 4.3 | 42.6 | 7.2 |
| Hemac-gel | 16 | 45 | ACD | 0 | 3 | 98.7 | 11.2 | 58.3 | 12.6 | 57.3 | 6.7 |
| | 12 | 45 | ACD | 0 | 3 | 85.0 | 5.4 | 54.3 | 12.3 | 31.3 | 7.6 |
| | 8 | 45 | ACD | 0 | 3 | 83.3 | 4.0 | 51.0 | 15.1 | 38.5 | 8.0 |
| | 4 | 45 | ACD | 0 | 3 | 83.0 | 3.7 | 72.7 | 3.4 | 18.5 | 6.0 |
| | 16 | 45 | CPD | 0 | 3 | 63.0 | 10.6 | 89.7 | 3.1 | 36.8 | 12.6 |
| Gelofu-sine | 20 | 45 | CPD | 2 | 4 | 29.5 | 4.8 | 87.5 | 0.8 | 94.4 | 1.5 |
| | 16 | 45 | CPD | 2 | 3 | 44.7 | 2.4 | 79.3 | 2.9 | 70.5 | 14.2 |
| | 12 | 45 | CPD | 2 | 3 | 44.0 | 0.5 | 79.7 | 1.4 | 72.7 | 13.9 |
| | 8 | 45 | CPD | 2 | 3 | 38.0 | 3.3 | 72.7 | 2.8 | 63.0 | 14.0 |
| | 4 | 45 | CPD | 2 | 3 | 27.7 | 9.0 | 72.7 | 2.8 | 38.3 | 19.4 |

*Approximate
**Standard Error
In all Samples without modified fluid gelatin, cells had badly clumped. In samples suspended in CPD without gelatin, attempts to resuspend the clumped cells failed whether or not 0.2 mM adenosine was present.

TABLE 2

| Effect of Plasma Concentration | | | | | | | | | | |
|---|---|---|---|---|---|---|---|---|---|---|
| Modified Fluid Gelatin | Plasma | | Buffer | Adenosine | | Leukocyte Recovery % | | Viability % | | Bacterial Kill |
| Brand | % of Total | %* of Total | | (mM) | No. of Samples | | SE** | | SE | | SE |
| Plasma-gel | 12 | 45.0 | ACD | 0 | 12 | 72.1 | 4.9 | 66.6 | 5.3 | 68.3 | 4.8 |
| | 12 | 33.8 | ACD | 0 | 3 | 67.0 | 8.6 | 37.7 | 4.6 | 35.0 | 8.8 |
| | 12 | 22.5 | ACD | 0 | 3 | 69.3 | 6.9 | 20.0 | 0.5 | 27.5 | 8.7 |
| | 12 | 11.3 | ACD | 0 | 3 | 82.3 | 7.5 | 11.3 | 1.5 | 9.3 | 4.8 |
| | 12 | 0.0 | ACD | 0 | 3 | 74.0 | 6.1 | 17.3 | 4.7 | 9.0 | 3.7 |

*Approximate
**Standard Error

TABLE 3

| Effect of Adenosine | | | | | | | | | | |
|---|---|---|---|---|---|---|---|---|---|---|
| Modified Fluid Gelatin | Plasma | | Buffer | Adenosine | | Leukocyte Recovery % | | Viability % | | Bacterial Kill |
| Brand | % of Total | %* of Total | | (mM) | No. of Samples | | SE** | | SE | | SE |
| Plasma-gel | 12 | 45 | CPD | 0 | 6 | 62.7 | 7.4 | 81.8 | 4.3 | 42.6 | 7.2 |
| | 12 | 45 | CPD | 0.002 | 3 | 55.0 | 9.7 | 83.7 | 3.0 | 66.8 | 4.5 |
| | 12 | 45 | CPD | 0.02 | 3 | 61.3 | 8.4 | 85.7 | 2.3 | 55.0 | 9.0 |
| | 12 | 45 | CPD | 0.2 | 3 | 58.3 | 9.3 | 83.7 | 3.8 | 61.2 | 7.2 |
| | 12 | 45 | CPD | 2 | 6 | 62.0 | 4.6 | 86.0 | 1.5 | 68.8 | 6.2 |
| Hemac-gel | 16 | 45 | CPD | 0 | 3 | 63.0 | 10.6 | 89.7 | 3.1 | 36.8 | 12.6 |
| | 16 | 45 | CPD | 2 | 3 | 65.3 | 2.0 | 85.3 | 1.4 | 75.2 | 4.4 |
| Gelofu-sine | 20 | 45 | CPD | 0 | 1 | 61.0 | 0.0 | 84.0 | 0.0 | 20.0 | 8.5 |
| | 20 | 45 | CPD | 2 | 4 | 49.5 | 4.8 | 87.5 | 0.8 | 94.4 | 1.5 |

*Approximate
**Standard Error

Additional storage samples were prepared having compositions as shown in Table 4 below using the same procedures as described above with ACD as the buffer and leukocytes in each case at a concentration of $1 \times 10^8$ cells/ml.

These storage compositions were held for two weeks instead of 7 days at 4° C. After storage, leukocyte retrieval was facilitated by diluting the storage composition with an equal volume of phosphate-buffered saline, which reduced viscosity and facilitated accurate pipetting. Recovery and viability were measured immediately after dilution instead of after isolation and resuspension of the leukocytes, thus improving reliability of these measurements. In addition, the bacteria used in the bacteria killing assay were *S. aureus* strain 502A from the American Type Culture Collection. The results were as follows:

TABLE 4

| No. Samples | Modified Fluid Gelatin Brand | % of Total | Plasma %* of Total | Adenosine mM | Leukocyte % Recovery | | Viability % | | Bacterial Killing % | |
| --- | --- | --- | --- | --- | --- | --- | --- | --- | --- | --- |
| | | | | | | SE** | | SE | | SE |
| 6 | Plasmagel | 12 | 45 | 2 | 63.3 | 7.1 | 80.2 | 3.4 | 50.5 | 4.5 |
| 5 | Haemaccel | 16 | 45 | 2 | 53.7 | 4.5 | 94.6 | 1.8 | 94.6 | 1.7 |
| 6 | Gelofusine | 20 | 45 | 2 | 80.8 | 5.0 | 87.6 | 2.8 | 92.8 | 3.4 |

*Approximate
**Standard Error

Additional storage samples were prepared as described above having the composition:

| | Percent |
| --- | --- |
| Plasmagel | 12% |
| Plasma | 45% | containing ACD as the buffer and containing various concentrations of heterocyclic bases or of nucleosides, as shown in Table 5 below. After one week storage at 4° C. the leukocyte recovery, viability, and bacterial kill were determined as described above with the results shown in Table 5.

TABLE 5

| Heterocyclic Base | Concentration, mM | Leukocyte Recovery % | | Viability % | | Bacterial Kill % | |
| --- | --- | --- | --- | --- | --- | --- | --- |
| | | | SE | | SE | | SE |
| Adenine | 2.0 | 67.3 | 0.5 | 75.3 | 4.0 | 56.3 | 22.6 |
| Adenine | 0.2 | 72.3 | 8.2 | 72.7 | 3.7 | 37.0 | 30.4 |
| Cytosine | 1.0 | 68.7 | 11.5 | 90.7 | 5.8 | 75.3 | 18.7 |
| Uracil | 0.2 | 68.3 | 5.2 | 82.0 | 4.5 | 70.6 | 15.3 |
| Ribosylnucleoside | | | | | | | |
| Cytidine | 2.0 | 65.0 | 7.5 | 81.7 | 6.5 | 53.8 | 29.9 |
| Cytidine | 0.2 | 76.3 | 15.3 | 81.0 | 7.0 | 47.7 | 35.4 |
| Guanosine | 1.0 | 69.0 | 5.7 | 89.3 | 6.1 | 89.3 | 2.8 |
| Uridine | 1.0 | 66.3 | 13.1 | 86.0 | 14.1 | 83.2 | 6.5 |

Generally similar results can be obtained with various other free bases, nucleosides or nucleotides.

What is claimed is:

1. The method of stabilizing for storage leukocytes obtained from human blood which comprises mixing a suspension of said leukocytes in plasma with modified fluid gelatin and with a non-toxic buffer.

2. The method of stabilizing for storage leukocytes obtained from human blood which comprises suspending said leukocytes in plasma containing modified fluid gelatin and a non-toxic buffer.

3. The method as claimed in claim 1 wherein said mixture includes one or more of (a) the heterocyclic bases which occur in nucleic acids; (b) nucleosides containing said bases; or (c) nucleotides containing said bases.

4. The method as claimed in any of claims 1, 2 or 3 including in addition the step of storing said mixture for at least 24 hours at a temperature of 25° C. or below.

5. A composition for maintaining the viability and bactericidal capacity of human leukocytes during storage comprising 25 to 75% by weight of human plasma, an amount of modified fluid gelatin of from 4% by weight up to the amount causing the composition to gel at 40° C., a member of the group consisting of (a) the heterocyclic bases which occur in nucleic acids, (b) nucleosides containing said bases and (c) nucleotides containing said bases at a concentration from 0.001 to 5 mM, human luekocytes at a concentration from $10^7$ to $10^9$ cells per ml, and the balance a non-toxic aqueous buffer.

6. A composition as claimed in claim 5 in which said member is adenosine.

7. A composition for maintaining the viability and bactericidal capacity of human leukocytes during storage comprising 40–50 percent by weight of human plasma, 6–25 percent modified fluid gelatin, a nucleoside selected from the group of adenine or guanine at a concentration from 0.001 to 5 mM, human leukocytes at a concentration from $10^7$ to $10^9$ cells per ml, and the balance a non-toxic aqueous buffer.

* * * * *

UNITED STATES PATENT AND TRADEMARK OFFICE
CERTIFICATE OF CORRECTION

PATENT NO.   : 4,923,797
DATED        : May 8, 1990
INVENTOR(S)  : Bernard M. Babior It is certified that error appears in the above-identified patent and that said Letters Patent is hereby corrected as shown below:

On the title page, item [73]: This patent should be assigned to --Scripps Clinic and Research Foundation - La Jolla, California--, not "President and Fellows of Harvard College - Cambridge, Massachusetts.

In the Tables:

Table 1, column 5, line 18, delete "29.5" and insert therefor --49.5--.

Table 1, column 6, line 22, delete "72.7" and insert therefor --73.7--.

Signed and Sealed this

Fifteenth Day of October, 1991

Attest:

HARRY F. MANBECK, JR.

*Attesting Officer*         *Commissioner of Patents and Trademarks*